United States Patent [19]

Hatfield

[11] Patent Number: 4,663,097

[45] Date of Patent: May 5, 1987

[54] METHOD AND APPARATUS FOR CONTROLLING DYNAMIC INSTABILITY IN AXIALLY MOVING FORM

[75] Inventor: James H. Hatfield, Yarm, England

[73] Assignee: Imperial Chemical Industries, PLC., London, England

[21] Appl. No.: 768,143

[22] Filed: Aug. 22, 1985

Related U.S. Application Data

[63] Continuation-in-part of Ser. No. 656,467, Oct. 1, 1984, abandoned.

[30] Foreign Application Priority Data

Aug. 15, 1984 [GB] United Kingdom ............... 8420781
Oct. 15, 1984 [GB] United Kingdom ............... 8420761

[51] Int. Cl.$^4$ ........................................... B29C 47/92
[52] U.S. Cl. .................................. 264/40.7; 264/40.1; 264/40.5; 264/567; 425/135; 425/150
[58] Field of Search ............... 264/40.2, 40.4, 40.1, 264/40.7, 40.3, 40.5; 248/184; 425/135, 150

[56] References Cited

U.S. PATENT DOCUMENTS

| 4,101,612 | 7/1978 | Barker et al. | 264/22 |
| 4,201,741 | 5/1980 | Pannenbecker | 264/40.1 |
| 4,325,897 | 4/1982 | Zerle et al. | 264/40.3 |
| 4,243,363 | 1/1981 | Mulcahy | 425/140 |
| 4,355,966 | 10/1982 | Sweeney et al. | 425/140 |

FOREIGN PATENT DOCUMENTS

| 57-29438 | 2/1982 | Japan | 264/40.1 |
| 57-110907 | 7/1982 | Japan | 264/40.2 |
| 58-134713 | 8/1983 | Japan | 264/40.2 |

Primary Examiner—Jan Silbaugh
Assistant Examiner—Jennifer Cabaniss
Attorney, Agent, or Firm—Cushman, Darby & Cushman

[57] ABSTRACT

A method and apparatus for controlling induced dynamic instability in an axially moving form supported between two axially spaced supports wherein the form is relatively soft and therefore exposed to development of transverse tensional forces tending to pivot the form about one or both supports. Control is effected by establishing a datum axis, repeatedly sensing the lateral position of the form in at least two mutually inclined transverse directions, deriving signals proportional to the sensed lateral displacement of the form from the datum axis, converting the signals to thrust forces, and applying the thrust forces to restore the form to the desired lateral position. The technique is of particular value in the production of oriented polymeric tubular films.

12 Claims, 13 Drawing Figures

METHOD AND APPARATUS FOR CONTROLLING DYNAMIC INSTABILITY IN AXIALLY MOVING FORM

This application is a continuation-in-part of application Ser. No. 656,467, filed Oct. 1, 1984, now abandoned.

BACKGROUND OF THE INVENTION

1. Technical Field of Invention

This invention relates to a technique for controlling induced dynamic instability in an axially moving form, and, in particular, to a method and apparatus for effecting such control.

2. Background of the Art

In various industrial processes, including the manufacture of pipes, filaments and films, it may be desirable, or necessary, to expose a relatively rigid axially moving form to a treatment which will weaken the form and induce instability therein. For example, longitudinal orientation of a polymeric filament may be effected by feeding the filament at a controlled rate to an orientation zone in which the filament is softened by heating, and withdrawing the softened filament at an increased rate. Likewise, an oriented tubular film is usually produced by extruding a relatively thick-walled and rigid thermoplastics tube from an annular orifice, and subsequently stretching the extruded tube, at a temperature above the glass transition temperature (Tg) and below the melting temperature of the thermoplastics material, in the transverse and/or longitudinal directions to form a thin film, the stretching being effected in the transverse direction by means of internal gas pressure and in the longitudinal direction by withdrawing the tube at an appropriate rate in the direction of extrusion.

Temperature control during the heat treatment is of paramount importance and problems are generally encountered because of an apparent inability to achieve uniform heating around the form. While an extruded polymeric form is at relatively high temperature, the viscosity and tensile strength thereof are low and there is a tendency for the form to be positionally unstable and to wander randomly from side to side. Not only is the form liable to rupture while in this unstable condition, but the instability may lead to marked variations and irregularities in the thickness profile of oriented tubular film produced therefrom—rendering the resultant film commercially unacceptable.

Heating of an axially moving form to the desired treatment temperature is conveniently effected by an assembly comprising a plurality of infra-red heating elements disposed in a cylindrical array surrounding the form, and individual elements may be independently controlled in an attempt to overcome circumferential fluctuations in the thermal load of the heating assembly. Nevertheless, the problem persists that a significant proportion of commercially unacceptable film is produced, possibly as a consequence of external influences—such as exposure of the heated form to adventitious air currents in the vicinity of the production unit.

3. The Prior Art

Many attempts have been made to provide a solution to the problem of positional instability in polymeric tubular extrudates and of non-uniform wall thickness in films formed therefrom. For example, British patent GB No. 1440651 discloses a technique for controlling the cooling of a freshly extruded tube of a thermoplastics material, which may subsequently be stretched to yield an oriented tubular film, by feeding the tube, in the direction of extrusion, in heat-transfer relationship with an adjacent cooling surface, maintaining the cooling surface at a temperature below the melting point of the thermoplastics material, maintaining a sheath of a heat-transfer fluid between, and in contact with, the tube and the cooling surface, and cooling at least a selected area of the extruded tube by displacing the tube transversely of the direction of extrusion to decrease the thickness of the fluid sheath between the selected area and the cooling surface. In the production of tubular film the cooling surface is suitably a cooled, tapered mandrel located within the tube, and transverse displacement of the tube may be effected by a ring assembly comprising a plurality of rollers surrounding the tube.

British patent GB No. 1404947 discloses a technique for stabilising the position of a tubular film by passing a tubular film through an annular sleeve having a gas-permeable, convex arcuate surface disposed towards the film, and supplying gaseous fluid inwardly through the arcuate surface to create a cushion of gas between the film and arcuate surface to support the film out of contact with the surface.

British patent GB No. 2074349 discloses a technique for controlling the thickness of a blown tubular film in which film sectors of equal cross-sectional areas are allocated to corresponding tempering sectors of equal circumferential length on the die nozzle ring and the relevant tempering sectors of the nozzle ring are cooled to produce film in which the corresponding sectors are of the desired thickness or heated to produce film in which the corresponding sectors are of the desired thinness.

Despite these various proposals to control the cooling of a cast extrudate, to stabilise the position of a film bubble, and to effect differential temperature control of an annular extrusion die, the problem of positional instability in the production of tubular extrudates has not been overcome to the extent necessary to satisfy the increasingly stringent product quality standards demanded in the market place.

We have now devised an improved control technique.

SUMMARY OF THE INVENTION

The concept of the present invention stems from an appreciation that a relatively rigid form when moving axially between two spatially fixed supports will be rendered intrinsically unstable when softened, for example—by heating in an isokinetic environment at a location between the supports, and exposed to the development of transverse tensional forces. In particular, when the two supports, are substantially vertically spaced-apart the intermediate weakened section will permit the form to pivot about either or both of the supports somewhat in the manner of a mechanical metronome. Such instability is herein referred to as induced dynamic instability.

Accordingly the present invention provides a method of controlling induced dynamic instability in an axially moving form, the form being transversely fixedly located at an inlet forwarding station and at an axially spaced-apart outlet forwarding station, and being exposed at a location between the inlet and outlet stations to a treatment which will induce in the form a zone of dynamic instability, comprising:

establishing a datum axis indicative of the desired lateral position of the form, repeatedly sensing the lateral position of the form in at least two mutually inclined transverse directions at a sensing location upstream of the zone of induced dynamic instability, repeatedly deriving first and second signals proportional respectively to the sensed lateral displacement of the form from the datum axis in said at least two directions, converting said first and second signals to respective first and second thrust forces, and repeatedly applying said first and second thrust forces to the form in mutually inclined transverse directions at a location between the inlet forwarding station and the sensing location, to restore the form to the desired lateral position.

The invention also provides an apparatus for controlling induced dynamic instability in an axially moving form, the form being transversely fixedly located at an inlet forwarding station and at an axially spaced-apart outlet forwarding station, and being exposed at a location between the inlet and outlet stations to a treatment which will induce in the form a zone of dynamic instability comprising:

means for establishing a datum axis indicative of the desired lateral position of the form, sensor means for repeatedly sensing the lateral position of the form in at least two mutually inclined transverse directions at a sensing location upstream of the zone of induced dynamic instability, derivative means for repeatedly deriving first and second signals proportional respectively to the sensed lateral displacement of the form from the datum axis in said at least two directions, converter means for converting said first and second signals to first and second thrust forces, and actuator means for repeatedly applying said first and second thrust forces to the form in mutually inclined transverse directions at a location between the inlet forwarding station and the sensing location, to restore the form to the desired lateral position.

DETAILED DESCRIPTION AND PREFERRED EMBODIMENTS OF THE INVENTION

Figure 1:
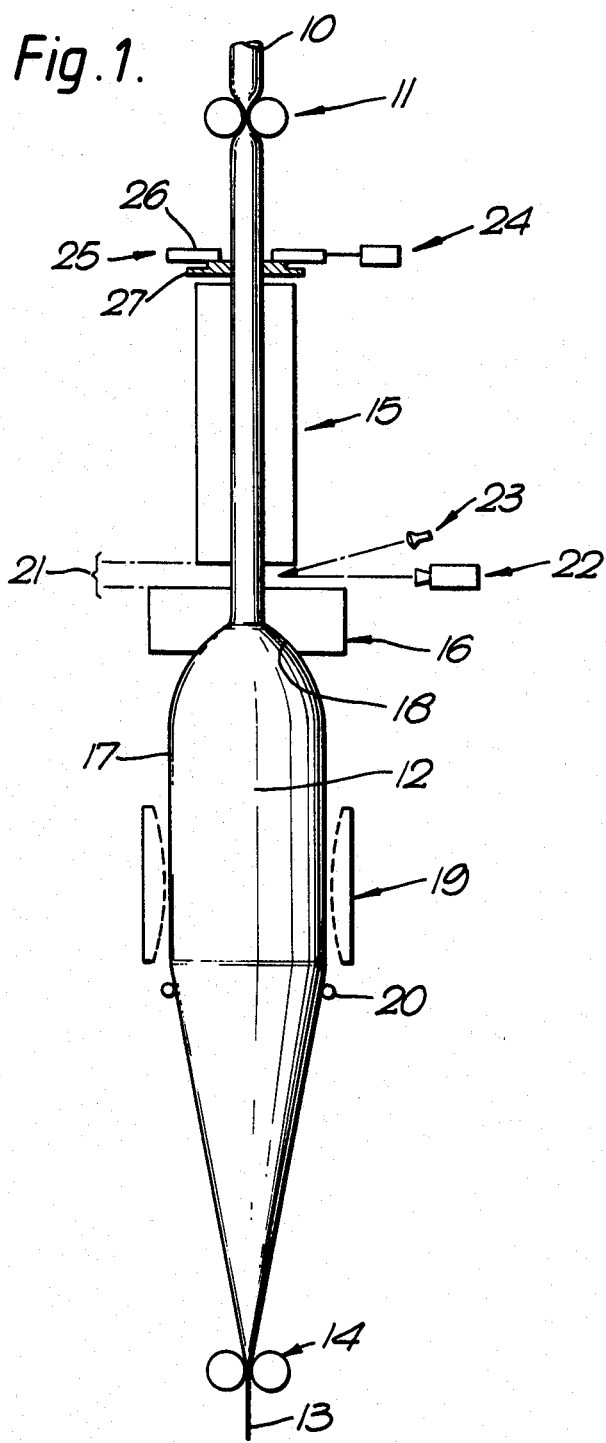

Although the invention is applicable to forms of various configurations including solid or substantially solid forms such as rods, filaments or threads, the technique is particularly suitable for controlling instability in tubular forms, especially substantially cylindrical tubular extrudates of the kind from which a biaxially oriented film can be produced on inflation and stretching by a conventional bubble film-forming process. For ease of description, the invention is hereinafter described by reference to such tubular film-forming extrudates, although it will be appreciated that other forss are within the scope of the invention.

Reference herein to movement of the form in an "axial" direction, unless otherwise stated, indicates movement substantially in the direction of the longitudinal axis of the form, and includes movement in a direction slightly inclined to said longitudinal axis, to accommodate the sway or wander normally experienced in conventional processes for the manufacture of tubular films. The form will desirably be disposed such that the longitudinal axis thereof extends in a vertical or substantially vertical direction. Reference to displacement of the form in a "transverse" or "lateral" direction indicates displacement in a plane normal or substantially normal to the longitudinal axis of the form.

The inlet forwarding station comprises means in a spatially fixed location for transporting the form in the axial direction while restraining the form against significant lateral movement. Forwarding may be effected passively, for example—the inlet forwarding station may comprise a die orifice from which the form is extruded in a forward, axial direction, or actively—for example, by means such as a pair of cooperating nip rolls or a pair of endless caterpillar belts, which engage a surface of the form to drive the form in the desired axial direction.

The outlet forwarding station will generally function in an active mode, and conveniently comprises spatially fixed means capable of gripping and withdrawing the form in an axial direction while preventing significant lateral displacemsnt of the form. Conveniently the outlet forwarding station comprises a pair of cooperating nip-rolls or endless belts.

In a preferred embodiment of the invention each of the inlet and outlet forwarding stations comprises a pair of cooperating nip rolls.

The selected datum axis is conveniently located on the central longitudinal axis extending between the inlet and outlet forwarding stations, although, if desired, the datum axis may be laterally displaced therefrom or inclined thereto. In a preferred embodiment of the invention a plurality of parallel or substantially parallel datum axes may be employed to indicate the desired lateral position of the form. For example, in the production of an oriented film from a tubular polymeric form the latter may be raised to the orienting temperature by passage through a bank of annular heating elements arranged within a cylindrical casing of greater internal diameter than the external diameter of the tubular form. Conveniently, therefore, two diametrically opposed points on the internal surface of the casing may respectively serve as the location for two datum axes extending in a longitudinal direction to define a spatial element within which the form is desirably maintained by appropriate lateral adjustment.

Although a datum axis need only comprise an imaginary spatial location, it may be desirable in practice to provide a visual representation of the selected datum axis (or axes). Such a representation may be generated conventionally—for example, electronically, as a cursor line on a visual display unit (VDU) and, if desired, may be superimposed upon a visual representation of the form on the VDU, thereby facilitating the task of the plant operators in setting up the production unit and also providing a control setpoint or target in relation to which the operators must endeavour to adjust and maintain the lateral position of the form.

Sensing the position of the form in each of the at least two mutually inclined transverse directions may be effected by contact means, such as a mechanical probe engaging a surface of the form. However, to avoid scratching, or otherwise damaging, the form it is preferred to employ a non-contact sensor. Non-contact sensing may be effected by any of a variety of techniques including ultrasonic scanning, capacitance measurements proportional to the dimensions of the annular gap between a form and a surrounding shield, observation of the shadow cast by the form relative to an appropriately positioned linear array of photodiodes, and pneumatic assessment by means of a pneumatic follower. However, for convenience, reliability and operator compatability it is preferred to employ a video camera to observe and sense the lateral position of the form.

Observation by video camera is conveniently effected by positioning a video camera with its line of sight directed towards the form in one of the at least two mutually inclined transverse directions, and in a plane substantially normal to the axial direction. A second video camera is similarly positioned in the second of the at least two mutually inclined transverse directions, conveniently in the same transverse plane as the first camera.

To facilitate electronic interpretation of the video image, the form, in the field of view of each video camera, may be illuminated—for example, by a light source, such as a light projector, associated with each camera. To achieve a high visual contrast between the form and its surroundings, each light source may be arranged to exploit parallax whereby the form, but not the background, is illuminated at an axial level corresponding to the line selected from the raster field of the associated camera for electronic interpretation, as hereinafter described. Parallax illumination is conveniently achieved if each light source is displaced axially and circumferentially (and, optionally, transversely) relative to the associated camera. Displacement of the light source in this way also reduces or avoids magnetic interference between the light source and its associated camera.

Conveniently, each light source is axially spaced apart from its associated camera to provide a small (e.g. up to 10°, and preferably about 4°) angle of inclination between the respective lines of sight of the camera and light source. If desired, each light source may be provided with a slit mask to provide a collimated light beam, such that the illumination is concentrated on the form in a relatively narrow axial band, axially spaced apart a small distance (e.g. 3 inches; 76 mm) from a similar illuminated band produced by the other mutually inclined light source(s). The axial dimension of each axial band is conveniently in a range of from 0.1 d to 0.3 d, particularly about 0.15 d, where d is the diameter of the form at the sensing location.

An image of the form observed by each video camera is conveniently displayed on an associated visual display unit (VDU) monitor. If desired, a single VDU monitor may be employed, the form image derived from each camera being sequentially displayed thereon by appropriate switching.

Any type of video camera may be employed, for example—a video camera having a raster field of 312 lines, one of which lines is selected for electronic interpretation as a means of sensing the lateral position of the form relative to the established datum axis. A different line is selected from the raster field of each camera, thereby ensuring that the form position is sensed at different axial locations by the respective cameras. Repetitive up-dating of the video field may be effected electronically at a suitable frequency—for example 50 Hz. A signal, in either analogue or digital format, proportional to the lateral position of the form relative to the established datum axis, may be derived by the aforementioned electronic interpretation of the selected line from each raster field, and employed, as hereinafter described, to control the lateral position of the form in the appropriate transverse direction.

It will be appreciated that a stream of analogue or digital signals is derived from each camera—first signals from one camera, second signals from the second camera, and so on, and the respective series of first and second signals may be electronically synchronised so that consequential displacement of the form in each of the mutually inclined directions occurs either simultaneously or sequentially, as desired.

As hereinbefore described, a representation of the selected datum axis or axes may be generated as a cursor line or lines superimposed on an image of the form on the VDU monitor. Conveniently, an additional cursor line, in a plane substantially normal to the datum axis or axes, is superimposed on the VDU monitor to indicate the axial location at which each camera senses the position of the form. The additional cursor line corresponds to the line selected for electronic interpretation from the raster field of the associated camera.

The lateral position of the form is sensed at a location upstream, relative to the direction of axial movement, of the zone of dynamic instability induced in the form. In the case of oriented tubular polymeric film production, this sensing location is conveniently situated adjacent the shoulder of the film bubble which develops in the orienting zone.

Although sensing of the lateral position of the form may be effected in a plurality of mutually inclined transverse directions, in general it is sufficient to sense the position in only two transverse directions, conveniently mutually orthogonally inclined.

The derived signal, from each camera, proportional to the lateral position of the form relative to the established datum axis, is suitably converted to a thrust force by conventional means—for example, by feeding the signal to a signal converter which, in turn, activates a drive mechanism such as a drive screw or worm mechanism, or a hydraulic or pneumatic positioning cylinder, capable of displacing an actuator to restore the form to the desired lateral position.

Feedback control of the system is conveniently effected by control means, such as a 3-term controller, installed between each video camera and the associated signal converter.

Displacement of the form to the desired lateral position is conveniently effected by an actuator assembly comprising a thrust member and a carrier therefor.

The thrust member may operate in a contact mode with a contact member, such as a plate, rod, bar or roller(s), bearing against an external surface of the form to effect the desired transverse displacement of the form relative to the datum axis. However, a non-contact mode of operation is preferred, and the thust member conveniently comprises a perforated surface whereby a gas, suitably air, may be discharged through the perforations at a rate and pressure sufficient to create a cushion of gas which will effect displacement of the form without damaging the surface thereof. A gas bearing having a circumferentially continuous, gas-permeable, perforated surface adjacent the form is particularly suitable.

The carrier comprises means for permitting movement of the thrust member in each of the mutually inclined transverse directions, and suitably includes a relatively rigid plate disposed in the transverse direction and having therein a suitably dimensioned orifice to permit axial movement of the form therethrough. Lateral movement of the plate, and its associated thrust member, may be effected by mounting the plate on an assembly of linear bearings suitably aligned to permit movement in each of the mutually inclined transverse directions. An alternative mounting arrangement, which permits lateral, while restricting torsional, displacement of the plate, comprises suspending the plate by a plurality of universally jointed supporting members, for example, GKN BRD-23 series Cardan shafts (frequently described as propellor shafts). Thus, a plate supported by an axially disposed Cardan shaft located at each corner of a notional polygon, for example a triangle or rectangle, may be transversely displaced by an appropriately directed thrust force, the assembly of plate and Cardanshafts functioning in the manner of a parallelogram. In a still further arrangement the carrier may be provided with a gimbal support mounting, in the manner of a self-aligning bearing assembly conventionally employed to support a ship's chronometer.

The actuator assembly is located between the inlet forwarding station and the downstream sensing location, whereby the inherent stiffness of the form upstream of the zone of induced dynamic instability may be exploited to transmit the transverse thrust force applied by the thrust member to a remote downstream location at which it is desired to control the lateral position of the form. In effect, the inlet forwarding station serves as a pivot point and the relatively rigid portion of the form acts as a cantilevered beam.

The extent of transverse movement of the actuator assembly in each of the mutually inclined transverse directions need only be small —for example, the mean displacement of the form from a central datum axis will generally not exceed 0.5 d, and preferably will be less than 0.25 where d is the diameter of the form. In practice, the required corrective displacement of a extruded cast polymeric tube in the production of an oriented tubular film may be even less—for example, of the order of 1 mm.

The general principle of the system according to the invention is that rapid corrections of deviations from coaxiality may be effected, thereby ensuring that any deviation is corrected while it is still small, and, that, consequentially, the thrust force required to achieve the desired correction is also small. Thus, mechanical feedback of a corrective measure may be effected with an inertial delay of less than 0.5 seconds, and generally less than 0.2 seconds.

Although forms of various configurations are susceptible to control in accordance with the invention, the herein described technique is of particular value in relation to the production of tubular films from any thermoplastics film-forming polymeric material, and particularly in the production of oriented films from crystalline or crystallisable polymers. For example, polymers and copolymers of 1-olefines, such as high density polyethylene, polypropylene or ethylene propylene copolymers, of polybutene-1, of poly-4-methylpentene-1, of polyesters such as polyethylene terephthalate and polyethylene-1,2-di-phenoxyethane-4,4'-dicarboxylate, of polysulphones, and of polyamides may be processed. A suitable film-forming material is a high molecular weight stereo-regular predominantly crystalline polymer of propylene, either in the form of a homopolymer or copolymerised with minor quantities (e.g. up to 15% by weight of the copolymer) of other unsaturated monomers, such as ethylene. Coated films and multiple-layer coextruded films may also be processed.

In the production of oriented tubular films in accordance with the invention significant improvements in film quality (thickness profile) and output are observed. In addition, a significant reduction in scrap film is achieved by virtue of the ability to reduce the width of edge-trims removed when the film bubble is slit to yield two independent flat films.

Figure 2:
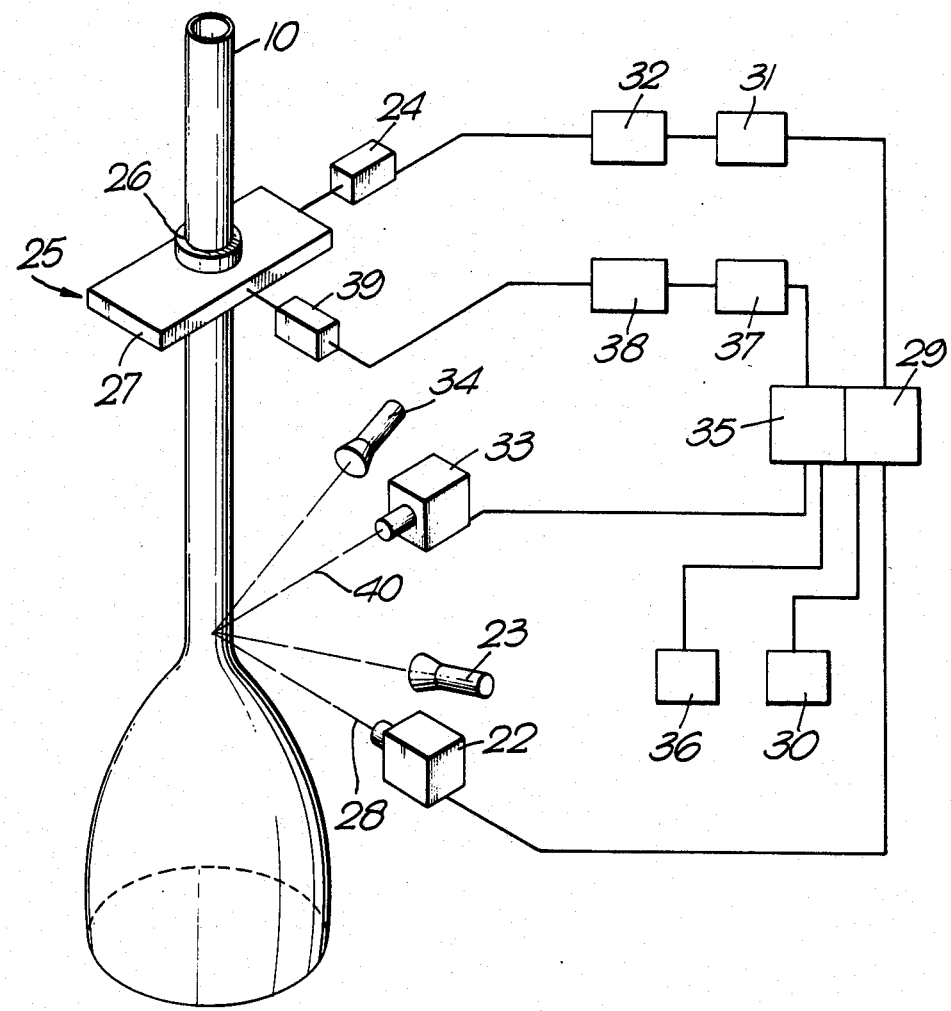
Figure 3:
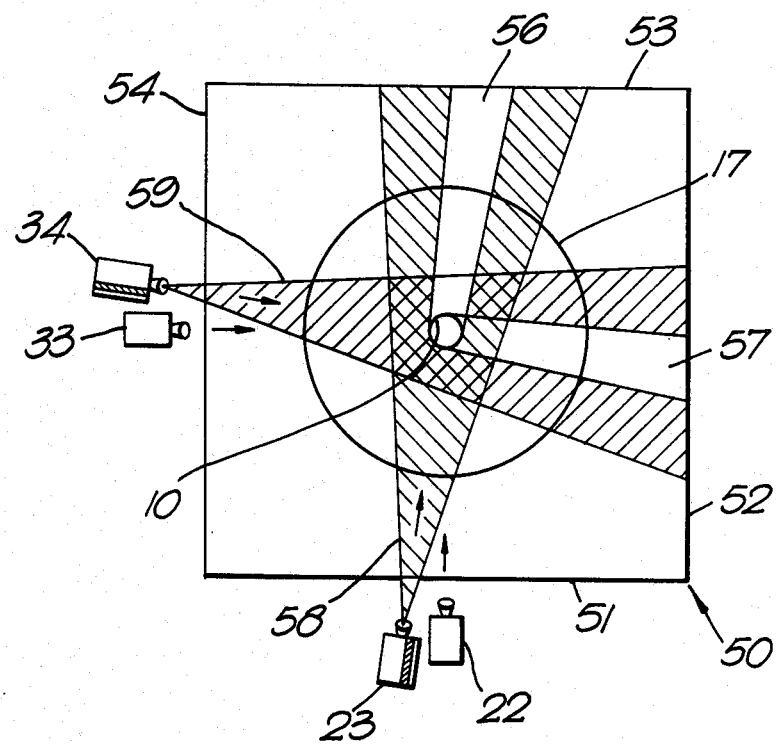
Figure 4:
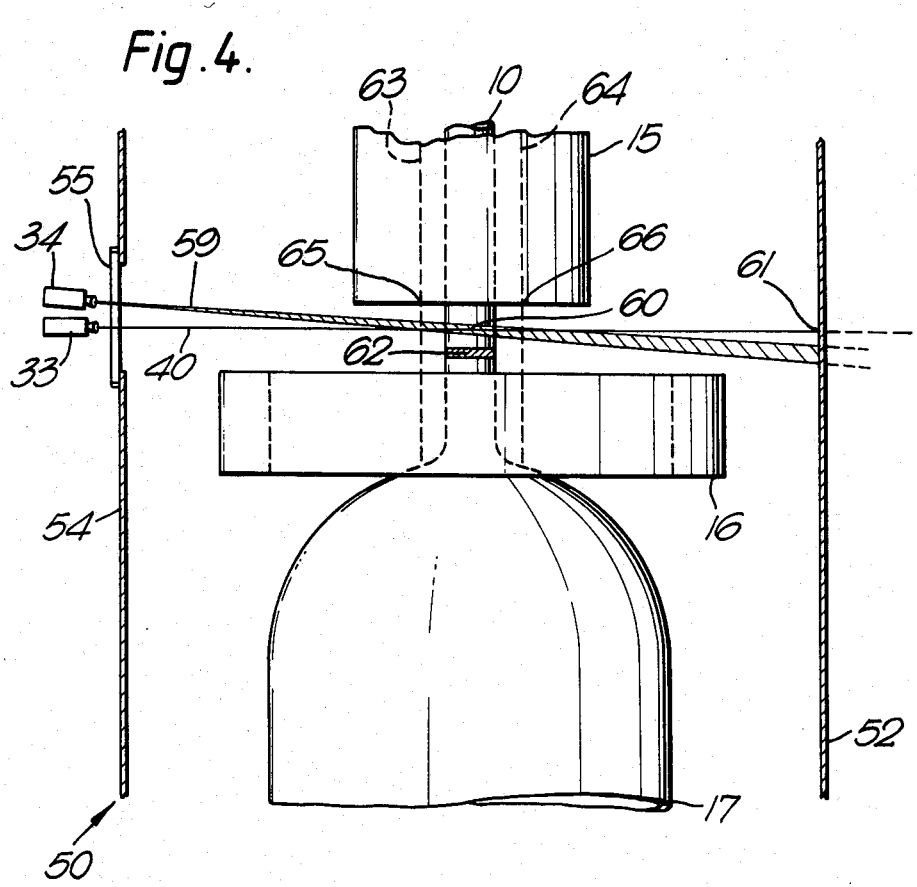
Figure 6:
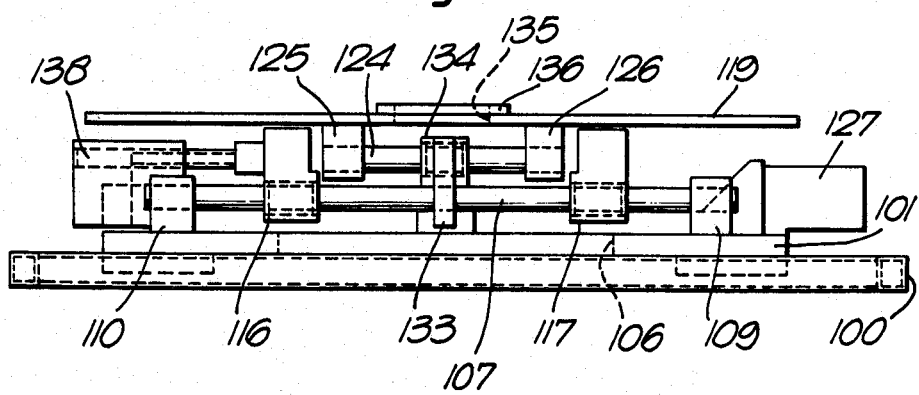
Figure 5:
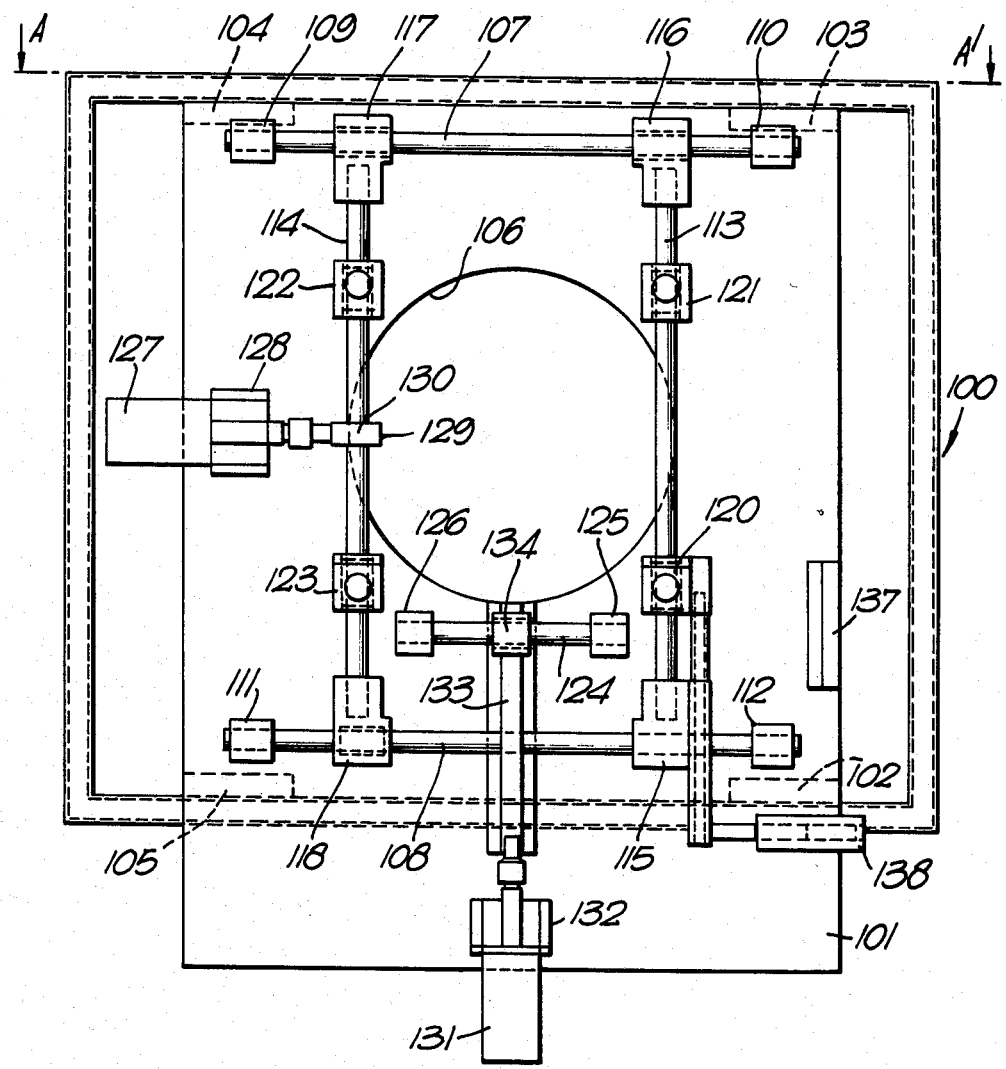
Figure 7:
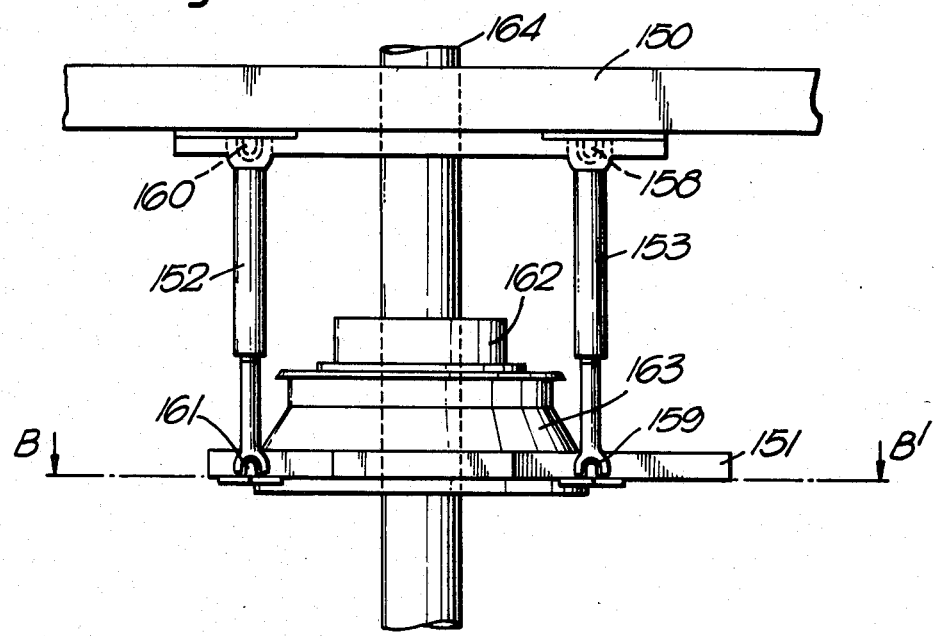
Figure 8:
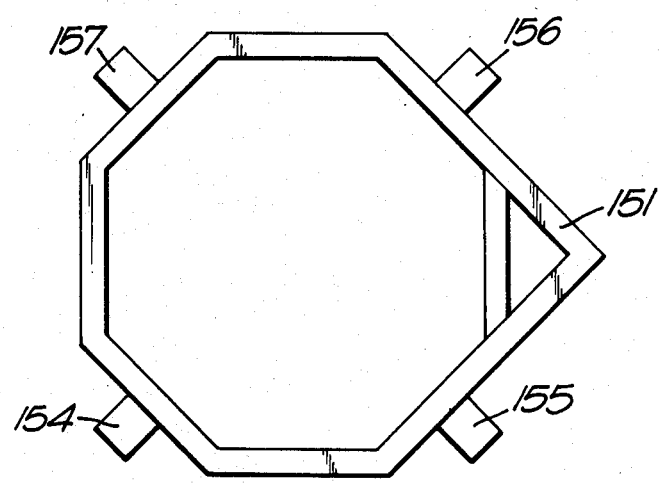
Figure 9:
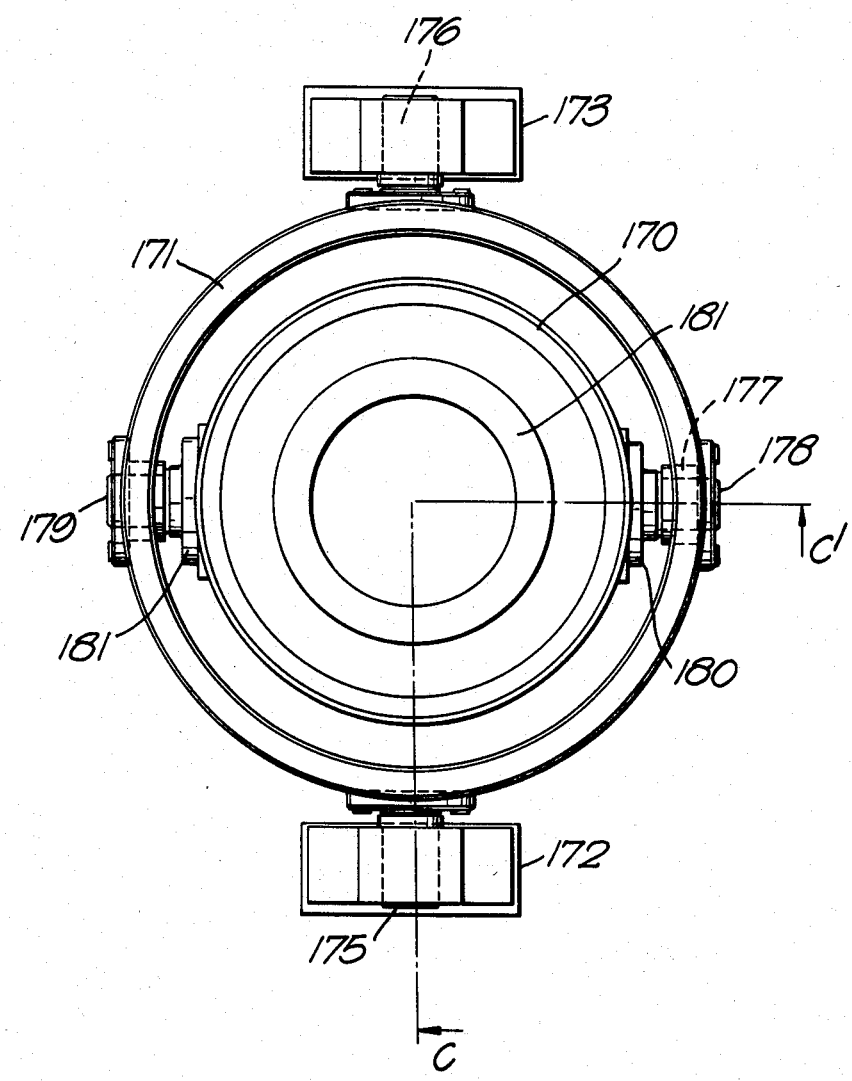
Figure 10:
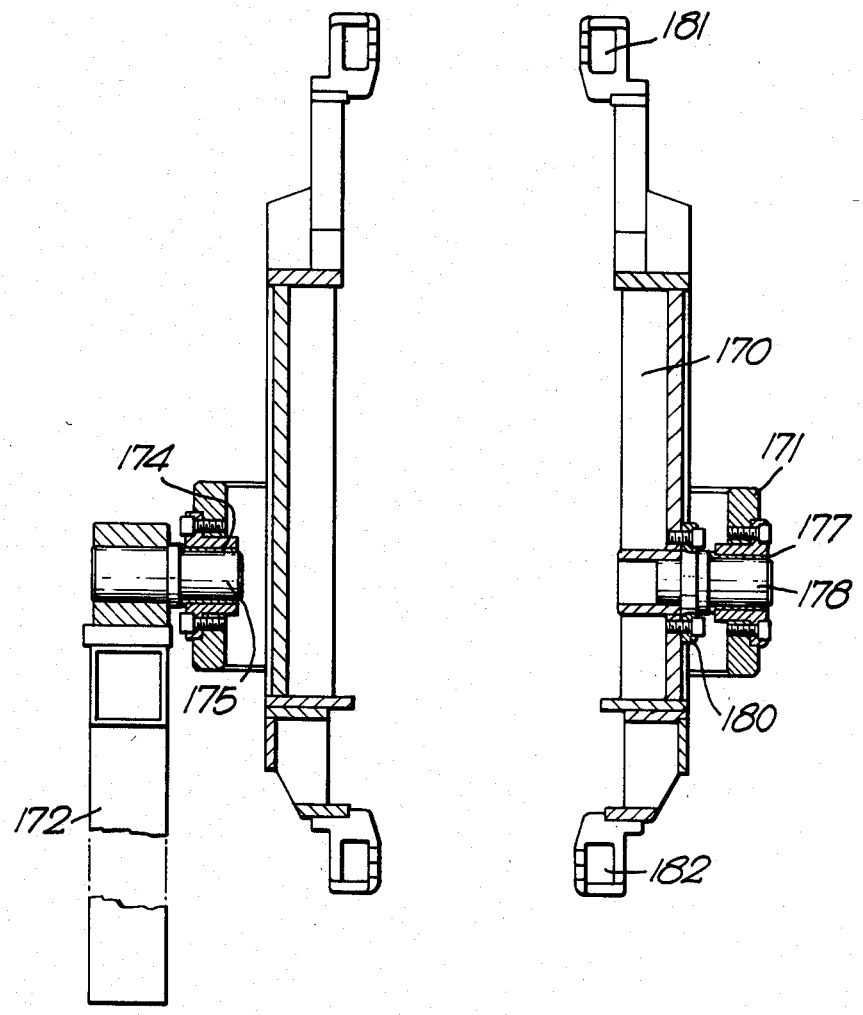
Figure 11:
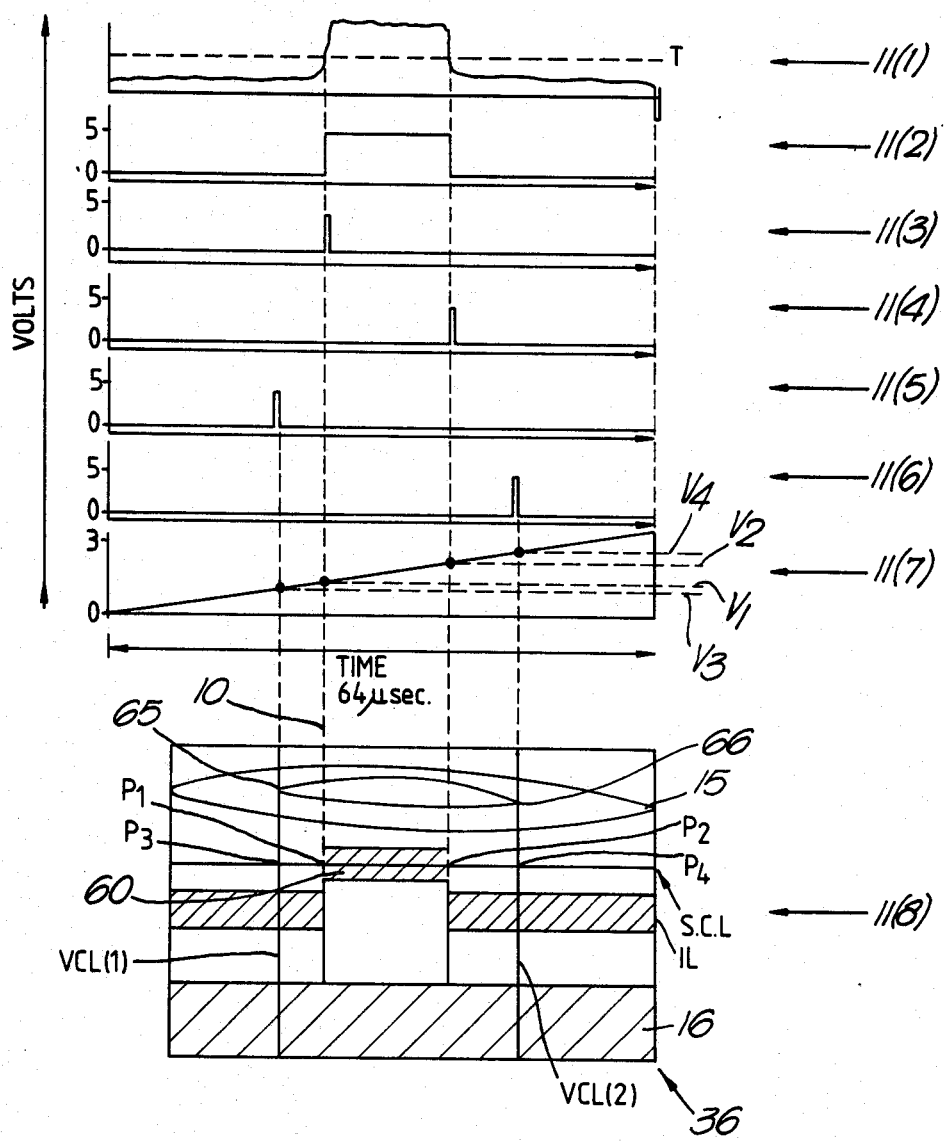
Figure 12:
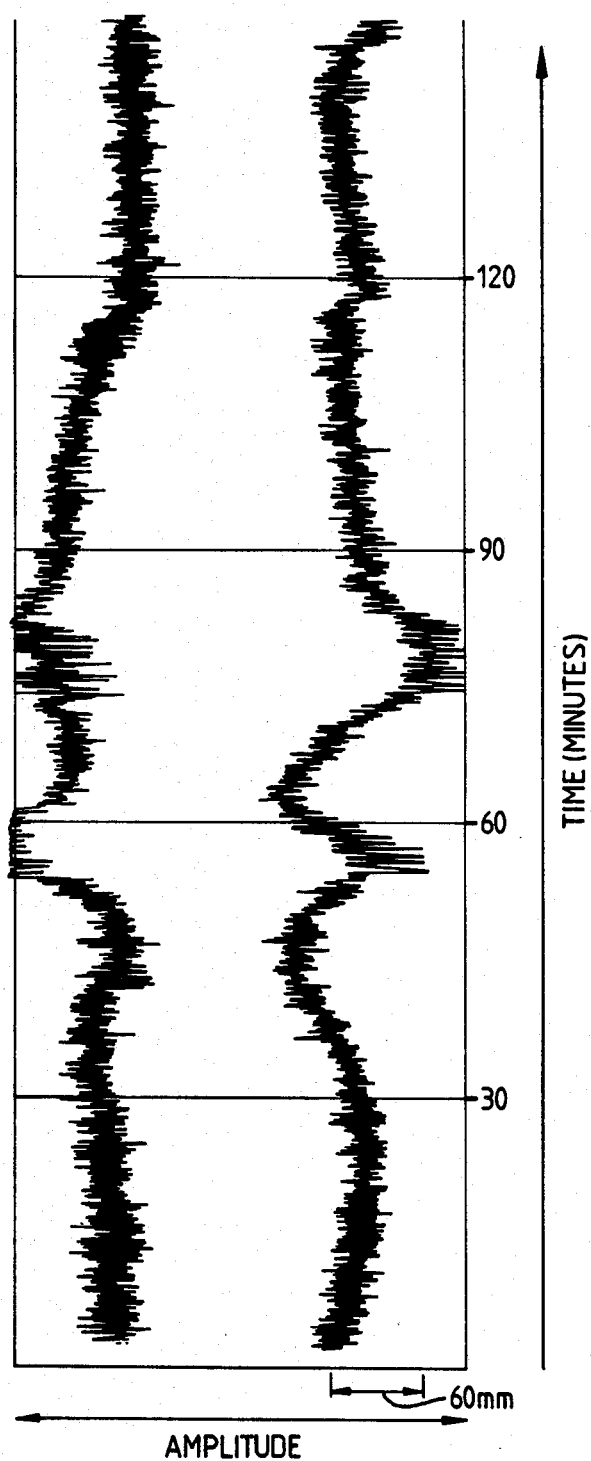
Figure 13:
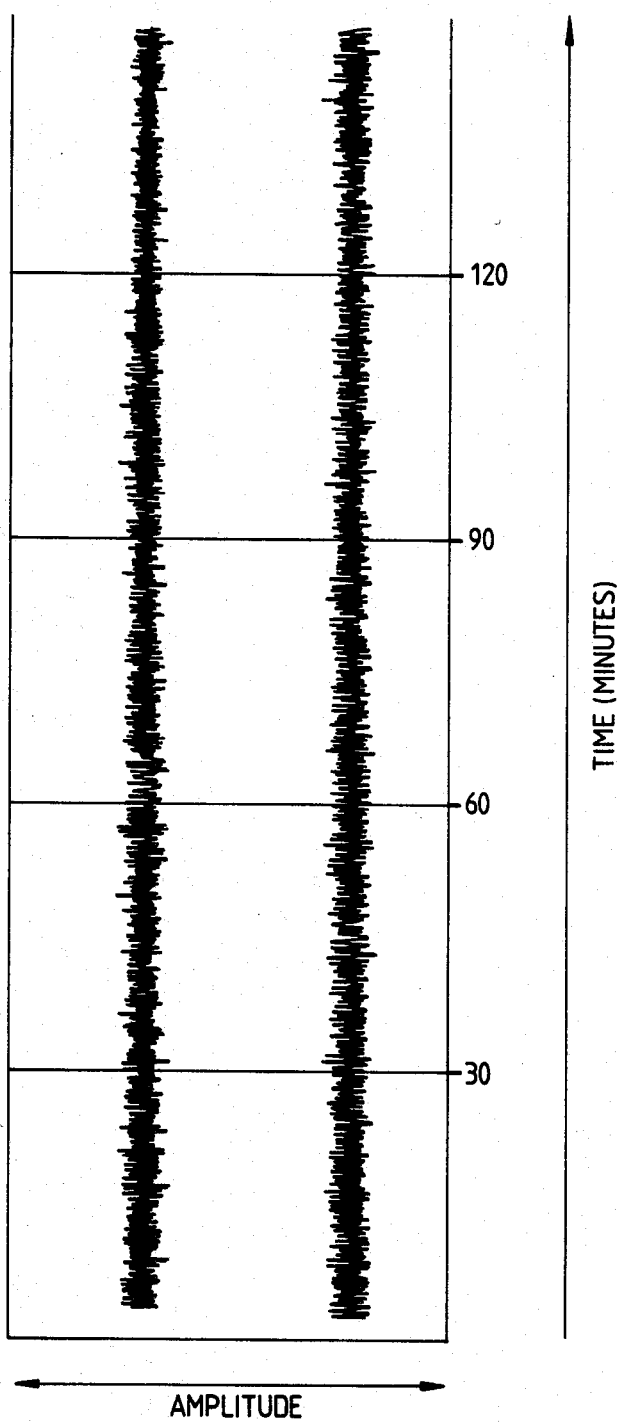

The invention is illustrated by reference to the accompanying drawings in which:

FIG. 1 is a schematic side elevation (not to scale) depicting the production of a biaxially oriented tubular film from a polymeric form the induced instability of which is controlled in accordance with the invention, FIG. 2 is a schematic fragmentary perspective view depicting a video camera assembly for sensing the lateral position of an unstable tubular form and a feed-back system to an actuator assembly for controlling the instability, FIG. 3 is a schematic plan view of the video camera and associated form-illuminating assembly, FIG. 4 is a schematic side elevation normal to the field of view of one of the video cameras and its associated light source, FIG. 5 is an inverted plan view of the transverse displacment mechanism for the carrier plate of the actuator assembly, FIG. 6 is a side elevation (not to scale) along the line A-A$^1$ of FIG. 5, FIG. 7 is side elevation of an alternative support assembly for a transversely displaceable actuator assembly, FIG. 8 is a plan view of the actuator carrier frame along the line B-B$^1$ of FIG. 7, FIG. 9 is a schematic plan view of a gimbal-mounted actuator assembly, FIG. 10 is a notional segmental side elevation along the line C-C$^1$ of FIG. 9, FIG. 11(1) to 11(8) inclusive illustrates the electronic interpretation of the video signals from a camera, FIG. 12 is a pen-recorder chart with traces reflecting the comparative instability of a form in the production of tubular film, and FIG. 13 depicts similar traces illustrating the improved form stabiiity achieved by use of a control system in accordance with the invention.

Referring to FIG. 1 of the drawings, a relatively rigid thermoplastics polymeric cast tube 10, which has been extruded from an annular die orifice (not shown) and quenched by an internal mandrel and external bath assembly (not shown) of the kind described in British Patent GB No. 1284321, is axially forwarded at an inlet forwarding station comprising a pair of cooperating nip rolls 11 which grip the tube and forward it in an axial direction at a controlled speed while preventing transverse displacement thereof. Nip rolls 11 only partially collapse cast tube 10 to permit the axial introduction of an inflating gas, such as air, to expand the tube in a downstream orienting zone, generally designated 12, from which lay-flat oriented tubular film 13 is axially withdrawn at an outlet forwarding station comprising a pair of cooperating nip rolls 14. Nip rolls 14 rotate at a peripheral speed in excess of that of inlet nip rolls 11 to effect longitudinal orientation of the tube, and substantially completely collapse the oriented tubular film to prevent escape of the inflating gas therefrom. Nip rolls 14 are spatially fixed to prevent transverse displacement of the tubular film in the vicinity of the outlet forwarding station.

The temperature of the quenched cast tube 10 is progressively increased in a cylindrical heater assembly 15, and in an axially spaced apart stabilizer heater 16, whereby the polymeric tube is softened, and then expanded by the pressure of the internal inflating gas to form a bubble 17. The softened shoulder region 18 of the bubble constitutes a zone of induced dynamic instability, as hereinbefore described, despite the lateral restraining influence exerted both by a perforated-arcuate air cooling and stabilising ring 19 of the kind disclosed in British patent GB No. 1404947, and by convergence guide rolls 20.

At a sensing location upstream (relative to the axial direction of extrusion) of the zone of induced dynamic instability, conveniently in the axial gap 21 between heaters 15 and 16, a first video camera 22 is arranged to view the cast tube in a plane normal to the longitudinal axis of the form extending between pairs of nip rolls 11 and 14, the field of view of the camera being illuminated by an associated light source, such as a projector 23, slightly inclined relative to said plane.

As hereinafter described, a selected line from the raster field of video camera 22 is electronically interpreted to derive a series of signals respectively proportional to the instantaneous lateral position of the cast tube relative to the central longitudinal axis thereof (the datum axis), and these signals are channeled through a feed-back control loop to activate a thrust device, such as a pneumatic positioning cylinder 24, which in turn effects transverse displacement of an actuator 25 comprising an air-bearing 26 mounted on a transversely displaceable carrier plate 27. As shown more clearly in FIG. 2, displacement of actuator assembly 25 is effected transversely in an orthogonal direction relative to the line of sight 28 of camera 22.

Referring to FIG. 2 of the drawings, a video interpreter 29 enables the image of the cast tube observed by camera 22 to be displayed on a VDU monitor 30, and electronically interprets the selected line from the raster field of camera 22, the resultant derived signal being fed to a feedback control assembly comprising a 3-term controller 31 and thence to an electro-pneumatic signal converter 32 thereby to drive the pneumatic positioning cylinder 24.

A second video camera 33, orthogonally inclined relative to camera 22, observes the cast tube in the sensing location illuminated by associated projector 34, a video interpreter 35 enabling the resultant image of the cast tube to be displayed on VDU monitor 36, and electronically interpreting a different line selected from the raster field of camera 33, the resultant derived signal being fed to a 3-term controller 37 and thence to an electro-pneumatic signal converter 38 thereby to drive a pneumatic cylinder 39 to effect transverse displacement of actuator assembly 25 in an orthogonal direction relative to the line of sight 40 of camera 33.

The arrangement of the cameras and associated light sources is illustrated in FIGS. 3 and 4. The bubble 17 is enclosed within a generally cubical cubicle 50, having four axially disposed walls 51, 52, 53, 54, to provide thermal stability and prevent contamination in the vicinity of the bubble. A transparent window 55 (only one shown; FIG. 4) in each of two adjacent side walls 51, 54 of the cubicle provides a line of sight for each camera and associated light source. Cast tube 10 casts a shadow 56, 57 in the respective light beams 58, 59 generated by light sources 23, 34, and by suitably inclining each light source at a small angle (e.g. 4−) to the transverse plane in which the associated camera is located—to exploit parallax, the selected line from the raster field of that camera can be located at an axial level at which the cast tube is illuminated but the background (i.e. the internal surface of the opposed wall of the cubicle) is not illuminated thereby to improve the visual contrast between the tube and the background. Thus, referring to FIG. 4, light beam 59 from light source 34 is inclined to the horizontal (as drawn) such that the line of sight 40 of the selected line from the raster field of camera 33 is at an axial level corresponding with an illuminated band 60 on the cast tube and with an unlit portion 61 on the internal surface of wall 52 of the cubicle. Similarly, an illuminated band 62 (FIG. 4) is imposed on the cast tube by light source 23 at an axial level corresponding to the line of sight of the line selected from the raster field of camera 22.

FIG. 4 also illustrates the possibility of selecting two datum axes 63, 64 corresponding respectively to diametrically opposed locations 65, 66 on the internal surface of heater assembly 15. These datum axes together define a spatial element within which the lateral position of the cast tube should be maintained by controlling the dynamic instability induced therein.

FIGS. 5 and 6 illustrate one embodiment of a transverse displacement mechanism for the actuator assembly. FIG. 5 is a view from beneath the mechanism and depicts a generally rectangular supporting framework of girders 100 from which a sole plate 101 is suspended by brackets 102, 103, 104, 105. An orifice 106 is provided in the sole plate to permit axial passage therethrough of a form the position of which is to be controlled. A first pair of parallel shaft members 107, 108 is attached to the plate by pairs of support brackets 109, 110 and 111, 112 respectively. A second pair of parallel shaft members, 113, 114, orthogonally inclined to the first pair, is slideably mounted on the first pair of shaft members by pairs of bearing supports 115, 116 and 117, 118 respectively. A heat-shield plate 119 (see FIG. 6; not shown in FIG. 5) is slideably attached to the second pair of parallel shaft members by pairs of bearing supports 120, 121, and 122, 123 respectively. A further single shaft member 124 is fixedly attached to heat-shield plate 119 by support brackets 125, 126.

A first pneumatic positioning cylinder 127 is attached to plate 101 by support bracket 128 and is provided with a drive head 129 by which heat-shield plate 119 can be transversely displaced along shaft members 107, 108 on actuation of pneumatic positioning cylinder 127. Drive head 129 incorporates a coupling 130 by which the drive head is secured to shaft member 114.

A second pneumatic positioning cylinder 131 is attached to plate 101 by support bracket 132 and is provided with a drive arm 133 incorporating a bearing 134 to permit free passage therethrough of single shaft member 124, when positioning cylinder 127, is actuated to effect transverse displacement of heat-shield plate 119 along shaft members 107, 108.

Actuation of positioning cylinder 131 effects orthogonal transverse displacement of heat-shield plate 119 on bearing supports 120, 121, and 122, 123 running respectively on shaft members 113, 114. Heat-shield plate 119 is therefore capable of simultaneous or sequential transverse displacement along orthogonal axes.

An orifice 135 is provided in heat-shield plate 119 to permit the axial passage therethrough of a form the position of which is to be controlled. A strengthening ring 136 (FIG. 6) on the underside of the heat-shield plate provides support for an air-bearing (not shown) mounted on the upstream surface of the heat-shield plate (i.e. between the sole plate and heat-shield plate) to control the lateral position of the form. Air to support the form within the air-bearing is supplied from a manifold 137 by suitable connecting means (not shown) to a supply assembly 138 and thence to the air-bearing.

An alternative embodiment of a transverse displacement mechanism for the actuator assembly is illustrated in FIGS. 7 and 8. From a girder framework 150, a braced heptagonal supporting frame 151 is suspended by four universally jointed Cardan shafts 152, 153 (only two shown in FIG. 7) respectively attached to lugs 154, 155, 156, 157 on frame 151. A universal joint coupling at each end of each shaft—for example, 158, 159 and 160, 161 (FIG. 7) permits lateral displacement of frame 151 in orthogonally inclined directions under the influence of transverse thrusts applied by appropriately positioned drive mechanisms (not shown). When transversely displaced, the downstream universal joint couplings describe an arcuate path and supporting frame 151 therefore undergoes a slight axial displacement in the upstream direction in addition to the transverse displacement.

An air-bearing 162, and associated housing 163, mounted on supporting frame 151 effects appropriate lateral displacement of a tubular form 164 passing axially therethrough.

A gimbal-mounted actuator assembly is illustrated in FIGS. 9 and 10. The assembly comprises a generally cylindrical chamber 170 which may, if desired, include means for heating a tubular form, passing axially therethrough, to an appropriate temperature. The chamber is located within a rigid support ring 171 which in turn is mounted on spatially-fixed rigid girder supports 172, 173. Bearings 174 (FIG. 10) enable ring 171, and associated chamber 170, to pivot about a first axis extending between stub axles 175, 176 respectively secured in girder supports, 172, 173. Similarly, bearings 177 enable the chamber to pivot relative to ring 171 about a second axis extending between stub axles 178, 179 respectively secured in mountings 180, 181 attached to chamber 170. The chamber is therefore capable of being tilted about each of two mutually perpendicular axes located in a plane substantially normal to the axial direction of movement of a form passing through the chamber. Such tilting may be effected in response to derived signals, as hereinbefore described, by appropriately positioned drive mechanisms (not shown) acting on the chamber.

Annular gas bearings 182, 183 respectively located at the inlet and exit ends of chamber 170 serve as non-contact thrust members whereby an axially moving form may be restored to the desired lateral position on actuation of the assembly.

FIGS. 11(1) to 11(8) inclusive illustrate the electronic interpretation of the signals from a video camera in relation to the image of the cast tube displayed on the associated VDU monitor. Thus, in FIG. 11(8), VDU monitor 36 displays an image of the downstream end of heater assembly 15 and the upstream end of heater assembly 16 (see FIG. 1) together with cast tube 10 passing therethrough, an axial band 60 on the tube being illuminated by light source 34 (see FIG. 4). A selected cursor line SCL representing the selected line from the raster field of camera 33 is imposed horizontally on the illuminated band on the cast tube image. Two vertical cursor lines VCL(1) and VCL(2) coincident with diametrically opposed locations 65, 66 on the internal surface of heater assembly 15 (see also FIG. 4) are also imposed on VDU monitor 36. The background in the region of axial band 60 is dark as viewed by camera 33, but the background at a slightly lower level is illuminated, IL, by light source 34, although the cast tube itself, as viewed by camera 33, appears dark at the lower level corresponding to band 62 (FIG. 4).

Electronic interpretation of the video signals from a selected camera is illustrated by reference to FIGS. 11(1) to 11(7) inclusive in which:

FIG. 11(1) depicts the video signal for a selected line from the raster field of the camera, the tails of the voltage plot representing the dark background, and the maximum level of the voltage plot representing the illuminated land on the cast tube, FIG. 11(2) depicts the thresholded signal obtained by comparing the video signal with a constant DC threshold voltage T (FIG. 11(1)), FIGS. 11(3) and 11(4) show timing pulses representing opposed edges of the cast tube, FIGS. 11(5) and 11(6) illustrate the production of vertical cursor lines, and FIG. 11(7) illustrates the sampling of a sawtooth voltage ramp.

The illustrated circuit embodiment functions as follows:

A master clock signal (suitably 4.0 MHz) is used to drive an 8-bit counter chain. This first running count is continuously digitally compared with a first normally static 8-bit count and when parity occurs the video monitor output is switched from 'video' to 'white level'. This effectively puts a spot on the current line of the raster field. In addition, when parity occurs, a "sample and hold" circuit samples a sawtooth voltage ramp, voltages V3 and V4 (FIG. 11(7)) corresponding to positions P3 and P4 across the video picture (FIG. 11(8)). The process is repeated for each line in the raster field, so creating in effect a vertical white cursor line, the position of which (P3) is revealed by the (suitably filtered) voltage (V3) obtained from the "sample and hold" circuit. A second static 8-bit count is also compared with the first running count to produce a second vertical cursor line (position P4; voltage V4). The analogue mean of the two voltages V3 and V4, i.e. (V3 +V4)/2, is taken, corresponding to the position of a line exactly central between the two vertical cursor lines, and this is passed to one of the 3-term controllers as a "remote set-point" signal.

Thus, in effect, the two vertical cursor lines define a setpoint (or target) for control purposes.

On completion of the running 8-bit count, the count is recommenced at zero and a line synchronization pulse (signal) is generated and sent to the video camera to cause the scan to reset and commence the next line.

The line synchronization signal also resets the sawtooth voltage ramp to zero volts.

The 4.0 MHz clock signal is also divided by 80,000 to obtain a 50 Hz signal which is sent to the video camera as a frame synchronization pulse every 20 msec.

The line synchronization signal is also itself passed to a second running 8-bit counter which is continuously compared with a third normally static 8-bit count. When parity occurs, the video output is again switched from 'video' to 'white level'. This has the effect of putting a single horizontal white line (the selected cursor line SCL, FIG. 11(8)) on the raster field. A suitable method is adopted to prevent blanking of the line and frame pulses. The single horizontal white line is termed the selected line.

The video signal is continuously compared with a constant DC voltage (the threshold T; FIG. 11(1)) using a fast comparator. This gives a signal in which a logic 0/1 transition occurs on the left hand edge of the form in the field of view and a logic 1/0 transition occurs on the right hand edge of the form. This operation is enhanced by the use of suitable parallax lighting conditions so that, for the chosen line, the form is seen as a brightly lit object against a dark background.

Timing pulses are generated from the left and right edges of the logic signal representing the position of the form—by the use of suitable monostable circuits.

The timing pulses are used to generate voltage signals (V1; V2) corresponding to the positions (P1; P2) of the edges of the form in the video picture—again by using a suitable "sample and hold" circuit to sample the saw-tooth voltage ramp—but in this case the sampling is gated by the selected line signal so that updating of the voltages V1 and V2 occurs only during the time when the camera scans the selected line i.e. at intervals of 20 msec.

The analogue mean of the two voltages V1 and V2, i.e. (V1 + V2)/2 is taken, corresponding to the position of the centre line of the form at an axial height in the picture corresponding to the selected line. This information is updated at 50 Hz (field rate) and, with suitable filtering, is passed to the 3-term controller as the "process variable" signal.

The positions of the two vertical and one horizontal cursor lines may be altered by slow clocking of the (normally static) counts presented to the digital comparators. By this means the control target position (setpoint) may be adjusted.

The significance of taking the analogue mean of the voltages representing the two edges of the form is that the mean is substantially free from spurious effects due to perspective when the form moves only or partly in a direction towards or away from the video camera.

The validity of the signal representing the position of the form is checked by counting the number of right hand edges (that is light/dark transitions) occurring on the chosen line. The signal is only validated and allowed to pass to the 3-term controller if the number of right hand edges is unity.

FIG. 12 illustrates a pen-recorder chart with traces representing lateral movement of a cast polymeric tube as observed by video cameras 22 and 33 during the production of a biaxially oriented tubular polyolefin film in accordance with Example 1, during which the control system of the invention was not operated. The respective traces depict movement of the cast tube in each of two orthogonal transverse directions generally designated East-West (E-W) and North-South (N-S).

Each transverse division on the chart represents a lateral displacement of about 6 mm, and it will be evident that over a period of about 140 minutes the cast tube suffered severe and continuous oscillation, relative to the longitudinal axis, in each of the E-W and N-S directions. In addition, the cast tube failed to maintain a true axial position, adopting varying inclinations to the vertical axis throughout the period of observation, as shown by the deviation from linearity of each trace.

In contrast, FIG. 13 illustrates E-W and N-S traces observed over a similar period on the same film production unit immediately after the installation and operation of a control system in accordance with the invention. The reduction in amplitude and the significant improvement in linearity of each trace demonstrates the dramatic improvement in cast tube stability achieved by the system of the invention. This improved stability was reflected in a considerable increase in yield of saleable film produced by the unit over a comparable period of time.

The invention is further illustrated by reference to the following Examples.

EXAMPLE 1

This is a comparative Example not according to the invention.

From an annular coextrusion die was extruded a composite triple-layer tube comprising a propylene homopolymer core having on each surface thereof a layer of a propylene-ethylene copolymer heat-sealable resin.

The tubular extrudate was quenched by an internal cooling mandrel and an external water bath, as described in British patent GB No. 1284321, the lateral position of the extrudate relative to the mandrel being controlled by a ring assembly comprising a plurality of rollers, as described in British patent GB No. 1440651.

The resultant relatively rigid cast tube, having a diameter of about 152 mm (6 inches) and wall thickness of about 0.94 mm (0.037 inch), was fed to a film-forming apparatus generally of the kind depicted in FIG. 1 of the accompanying drawings, the tube 10, being forwarded by cooperating nip rolls 11 through infra-red heaters 15, 16, where it was heated to a temperature of about 160° C., inflated by internal gas pressure to form a bubble 17, and withdrawn by cooperating nip rolls 14 to yield a biaxially oriented tubular film exhibiting a draw ratio of about 7:1 in each of the longitudinal and transverse directions and having a wall thickness of about 20 microns.

The lateral position of bubble 17 was stabilised by an arcuate air-bearing 19 of the kind described in British patent GB No. 1404947.

The video sensing and transverse position control system of the present invention was not operational other than that video cameras 22 and 33 (FIG. 2) were employed to derive signals indicative of the transverse position of the cast tube in each of the two mutually perpendicular directions at the sensing location. Pen-recordings, derived from these signals, representing bubble instability over a representative period of about 2.3 hours are displayed in FIG. 12, and it will be evident from the traces that the bubble exhibited considerable short term lateral instability (the amplitude of the trace) and inclination to the vertical axis (the deviation of the trace from linearity)—despite the operation of a roller ring control assembly (GB No. 1440651) and an arcuate stabilising sleeve (GB No. 1404947).

Film output from the unit was relatively low and considerable quantities of film had to be scrapped because of poor thickness profile.

EXAMPLE 2

The procedure of Example 1 was repeated save that the video sensing and transverse position control system of the invention was operational as hereinbefore described, using an actuator mechanism of the kind described with reference to FIGS. 5 and 6 of the drawings.

Pen-recorder traces of bubble stability over a representative period of about 2.3 hours are displayed in FIG. 13, and it will be evident therefrom that a dramatic improvement in stability was achieved by the control system of the invention.

Consequential upon the improved positional stability of the bubble, an increase in film production rate of about 17% was effected. In addition, the quality of the film produced was significantly improved (more uniform thickness profile).

To demonstrate the efficiency of the system a film production unit was closely monitored for two successive months (30 days) during 1984. During the first month the control system of the invention was not operated. In the second month, in which the control system was operated, the total output of commercially saleable film from the unit increased by 65% compared with that for the first month.

I claim:

1. A method for controlling induced dynamic instability in an axially moving form made of plastics material of indeterminate length as the form passes between first and second generally axially aligned supports which effectively guide the form throughout respective axially short segments of path so as to substantially determine within said segments the spatial location of said form transversally, translationally of a datum axis extending generally axially of said form, in an instance where said form is subjected to temporary softening all around the perimeter thereof at a zone of induced dynamic instability located axially between but axially short of said first and second generally axially aligned supports, so that within said zone said form tends to undergo transverse translational movement in relation to said datum axis in which said form moves generally metronomically, pivotally in respect to at least one of said support as a fulcrum for such movement, with a consequent deterioration in uniformity of the form as collected downstream of said zone and second support, said method comprising:

repeatedly sensing the lateral position of said form at at least two sites located axially between said first support and said zone of induced dynamic instability at a location at which said form is substantially less soft than is said form within said zone, these at least two sites being spaced angularly from one another about the perimeter of said form;

repeatedly deriving at least one signal from such repeated sensing, which at least one signal is proportional to the magnitude and direction of instantaneous deviation of said form from said datum axis;

juxtaposing at least one transversally-acting thruster with said form so as to enable said at least one thruster to repeatedly apply thrusts to said form at a location disposed axially between said first support and said location of said two sites at which said repeated sensing is conducted and operating said at least one thruster under control of said at least one signal to apply thrust forces to said form of at least one of such duration, number, magnitude and direction as to tend to maintain said form coincident with said datum axis within said zone of induced dynamic instability.

2. The method of claim 1, wherein:

said form is a tube of extruded thermoplastics polymeric film-forming material which is temporarily softened in said zone by being heated by application of thermal energy thereto, and which is being inflated in said zone, and which is being withdrawn by said second support at a rate which induces longitudinal orientation therein.

3. A method of producing a biaxially oriented tubular film, comprising:

extruding a tube of a thermoplastics polymeric film-forming material, quenching the extruded tube, reheating the quenched tube to an orienting temperature, thereby inducing in the tube a zone of dynamic instability wherein said tube is relatively soft and therefor exposed to development of transverse tensional forces tending to pivot said tube about one or both ends of said zone, inflating the reheated tube, and withdrawing the inflated tube at a rate which will introduce longitudinal orientation therein, the lateral position of the tube being controlled by:

axially moving said tube nominally along a datum axis between a transversally fixing inlet forwarding station and a transversally fixing outlet forwarding station which are spaced axially of one another with respect to said datum axis, while conducting said reheating, inflating and withdrawing, repeatedly sensing the lateral position of said tube in at least two mutually inclined transverse directions at a sensing location upstream of said zone of induced dynamic instability, repeatedly deriving first and second signals proportional respectively to the sensed lateral displacement of said tube from said datum axis in said at least two directions, converting said first and second signals to respective first and second thrust forces, and repeatedly applying said first and second thrust forces to said tube in mutually inclined transverse directions at a location between said inlet forwarding station and said sensing location, to restore the form to a greater degree of coincidence with said datum axis.

4. An apparatus for controlling induced dynamic instability in an axially moving form, the form being transversely fixedly located at an inlet forwarding station and at an axially spaced-apart outlet forwarding station, and being exposed at a location between the inlet and outlet stations to a treatment which will induce in the form a zone of dynamic instability wherein said form is relatively soft and therefore exposed to development of transverse tensional forces tending to pivot said form about one or both ends of said zone comprising:

means for establishing a datum axis indicative of the desired lateral position of the form, sensor means for repeatedly sensing the lateral position of the form in at least two mutually inclined transverse directions at a sensing location upstream of the zone of induced dynamic instability, derivative means for repeatedly deriving first and second signals proportional respectively to the sensed lateral displacement of the form from the datum axis in said at least two directions, converter means for converting said first and second signals to first and second thrust forces, and actuator means for repeatedly applying said first and second thrust forces to the form in mutually inclined transverse directions at a location between the inlet forwarding station and the sensing location, to restore the form to the desired lateral position.

5. An apparatus according to claim 4 wherein the sensor means comprises a video camera.

6. An apparatus according to claim 4 wherein the actuator means comprises a thrust member and a carrier therefor.

7. An apparatus acording to claim 6 wherein the thrust member comprises a gas bearing.

8. An apparatus according to claim 6 comprising linear bearings to permit movement of the carrier in each of the mutually inclined transverse directions.

9. An apparatus according to claim 6 comprising a gimbal-mounted support for the carrier.

10. An apparatus according to claim 4 comprising means for illuminating the form at the sensing location.

11. An apparatus according to claim 4 wherein at least one of the inlet and outlet forwarding stations comprises a pair of cooperating nip rolls.

12. An apparatus for producing a biaxially oriented tubular polymeric film comprising a control apparatus, comprising:

means including inlet and outlet transversally fixing forwarding stations, axially spaced from one another along a datum axis for forwarding a tube of extruded, quenched thermoplastics polymeric film-forming material axially nominally along said datum axis;

means for reheating the quenched tube to an orienting temperature, thereby inducing in the tube a zone of dynamic instability wherein said tube is relatively soft and therefore exposed to development of transverse tensional forces tending to pivot said tube about one or both ends of said zone and means for inflating the reheated tube, both at respective locations disposed intermediate said inlet and outlet transversally fixing forwarding stations;

said outlet transversally fixing forwarding station being adapted to axially advance said tube at such a greater speed than said inlet transversally fixing forwarding station as to introduce longitudinal orientation therein and said means for reheating and inflating being adapted to introduce transverse orientation in said tube;

means for establishing said datum axis, indicative of the desired lateral position of said tube;

sensor means for repeatedly sensing the lateral position of said tube in at least two mutually inclined transverse directions at a sensing location upstream of said zone of induced dynamic instability;

derivative means for repeatedly deriving first and second signals proportional respectively to the sensed lateral displacement of said tube from said datum axis in said at least two directions;

converter means for converting said first and second signals to first and second thrust forces; and actuator means for repeatedly applying said first and second thrust forces to said tube in mutually inclined transverse directions at a location between said inlet forwarding station and said sensing location, to restore the form to greater coincidence with said datum axis.

* * * * *